(12) United States Patent
Kawaguchi et al.

(10) Patent No.: US 6,395,533 B1
(45) Date of Patent: *May 28, 2002

(54) RECOVERING MICROORGANISMS FROM SOIL BY SUSPENDING SOIL IN A CITRATE BUFFER

(75) Inventors: Masahiro Kawaguchi; Etsuko Sugawa; Akira Kuriyama, all of Atsugi (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/433,212

(22) Filed: May 2, 1995

(30) Foreign Application Priority Data

May 2, 1994 (JP) .............................. 6-093272

(51) Int. Cl.$^7$ ............................. C12N 1/00; C12N 1/20; B09B 3/00
(52) U.S. Cl. ................... 435/252.1; 435/243; 435/261; 435/262.5; 435/264; 435/270; 435/822
(58) Field of Search ............................ 435/252.1, 261, 435/262.5, 264, 270, 822, 243

(56) References Cited

PUBLICATIONS

Ogiwara et al, "Regulation of Red–Violet Pigment . . . By A Pencillium Fungus", Bull Cell Agric . . . (48), 1991, pp. 30–37 Abstr.*

Imai et al, "Microb. degrad . . . ", Nippon Noyaku Gakkaishi (1986) 11(1), see abstract; AN 105:20444 CA.*

Steffan et al, Appl. Environ. Microb. 54(12) : 2908–2915 1988.*

Torsvik et al, Appl. Environ. Micro. 57(4) : 782–878(1990).*

Tsai et al, Appl. Environ. Micro. 57(4) : 1070–74 (1991).*

Pillai et al, Appl. Env. Micro. 57(8):2283–86(1991).*

Bruce et al, Appl. Environ. Microbiol. 58(10):3413–16, (1992).*

Holben et al., "DNA Probe Method for the Detection . . . Community" Appl. & Environ. Microb., vol. 54, No. 3, Mar. 1988, p. 703–711.

\* cited by examiner

*Primary Examiner*—David M. Naff
*Assistant Examiner*—Deborah K. Ware
(74) *Attorney, Agent, or Firm*—Fitzpatrick, Cella, Harper & Scinto

(57) ABSTRACT

Microorganisms are recovered from soil by suspending a soil sample containing the microorganisms in a buffer solution comprising an organic acid of 3 or more carbon atoms, and then separating the microorganisms into supernatant of the suspension. Furthermore, the citrate buffer is a citric acid and a salt of citric acid. Also microorganisms are separated from the soil particles and recovered from the suspension by centrifugation or electrophoresis.

13 Claims, No Drawings

RECOVERING MICROORGANISMS FROM SOIL BY SUSPENDING SOIL IN A CITRATE BUFFER

BACKGROUND OF THE INVENTION

1. Field of the Invention

The present invention relates to a method for recovering microorganisms from soil, and more specifically, it relates to a method for efficiently recovering microorganisms from soil with a good reproducibility by dispersing the soil containing the microorganisms in an organic acid buffer solution.

2. Related Background Art

In recent years, environmental pollution caused by hydrocarbons such as aromatic hydrocarbons, paraffins and naphthenes or organic chlorine compounds such as trichloroethylene has become a serious problem. Strongly desired are technologies to prevent further expansion of such serious environmental pollution and to purify and remedy the environment. Such technologies for soil environment remediation include physicochemical treatments, e.g., aeration, sun bleaching, vacuum vessel treatment, vacuum extraction, etc. However, these physicochemical treatments are not satisfactory for practical use, considering the operation cost, operability, energy consumption, treatment capacity, or that these treatments are to merely extract the pollutant and not to convert it to a harmless substance.

Therefore, much hope is laid on environment remediation utilizing microorganisms as a practical means in place of above physicochemical methods.

For example, in soil there have been found various kinds of microorganisms which can degrade soil-polluting, hardly degradable compounds such as aromatic hydrocarbons and organic chlorine compounds. Application of such microorganisms to the polluted soil to decompose the pollutants in the soil has been studied. Further, studies have been started on application of recombinant microorganisms having enhanced decomposing activity by genetic recombination techniques to soil.

To establish and popularize the environmental remediation methods utilizing microorganisms as a practical and socially effective technology, it is highly important to grasp growth and survival of the microorganism in the environment to which it is applied, as well as to develop various useful microorganisms.

In the agricultural production activity utilizing soil, it is also important to understand the activity, growth, propagation and survival of the original or introduced microorganisms in soil.

Many kinds of microorganisms are living in soil, but only small minority of these microorganisms have been identified, and most of them remain still unknown. In addition, for most of these microorganisms, even conditions necessary for their separation and culture have not been known. Isolation and identification of unknown microorganisms in soil are accompanied by many difficulties due to the specific environment, soil. This has been a main obstacle to the study of ecology of such microorganisms. Heretofore, contrivance and improvement in the separation and cultivation methods have been made to advance the ecological study of the soil microorganisms, but it is considered that there are many unknown microorganisms present in soil whose activity may be important in view of ecology. It is said that for only 0.1% or less of the total soil microorganisms, separation and cultivation methods have been established.

Therefore, it is one of the important tasks to grasp the ecology of the microorganisms which are hard to separate and cultivate, not only in the field of the applied technology such as soil remediation but also in fundamental science.

As a means for solving the above-mentioned problems, the following two methods are now under development in place of the conventional method problematically requiring a certain cultivation process to detect and count the microorganisms in soil:

(1) DNA analyzing method: a method in which DNA is isolated from the microbial cells and analyzed to study the microbial ecosystem in soil, and (2) Microbial particle detection method: a method in which the microbial cells themselves are separated from soil particles, and their ecosystem is then directly analyzed by the use of a fine particle measuring instrument such as a flow cytometer.

In above method (1), to use DNA as a detection means, it is necessary to recover the DNA of the microbial cells from a certain environmental sample. As a technique for recovering the microbial DNA from the soil, there are two methods available, a cell (microbial cell) recovery method and a direct cell lysis method.

The cell recovery method has a problem in that the recovery of the microbial cells from the soil greatly varies, depending upon the soil type and the kind of objective microorganism. For example, when microbial cells are recovered from soil, the recovery from one soil sample may be 40% or more, while that from another soil sample may be as little as 10% or more. This method has an advantage that the origin of the recovered DNA is definite and its purity is high, but the method has simultaneously a problem in that the amount of the recovered DNA is very small. For example, the amount of DNA obtained from 100 $\mu$g of soil by the conventional method is at most about 100 $\mu$g, and in some cases, it is as small as 1 to 2 $\mu$g. In consequence, there will occur a problem that the amount of DNA is not sufficient for analysis or it is so small that particular care must be taken for its handling.

On the contrary, the direct cell-lysis method has a feature that DNA is recovered in an amount of 1 to 2 mg per 100 g of soil, which is 10 to 100 times higher than the above-mentioned cell recovery method. It has a problem, however, that the target DNA is often contaminated with free DNA of unknown origin in soil, for example, those derived from dead bacteria, filamentous fungi, protozoans, plants etc. Such contamination interferes with the measurement of the objective DNA.

Accordingly, in order to utilize DNA analysis method as a detection means for the soil microorganisms, it is indispensable to recover the DNA of the target microorganism from soil. The prior techniques have, however, advantages and disadvantages as described above, and there is strongly required an extraction method of DNA from soil which can provide DNA of satisfying purity in a high recovery.

Also in above method (2), where microbial cells themselves are analyzed by detecting fine particles, the microbial cells must be recovered from soil, as in the above-mentioned method (1). Thus, the instability of the recovery rate of microbial cells becomes a serious problem.

In general, when microbial cells are separated from soil, the soil sample is first dispersed in pure water or a pH buffer solution (usually a phosphate buffer of about 100 mM and around pH 7 is used). At this point, the microbial cells are also dispersed in a dispersing medium to some extent, but if the sample is allowed to stand, most of the microbial cells cohere and precipitate together with the soil particles. The degree of this cohesion-precipitation is determined composit ely depending upon the type of soil (physical properties of the soil particles, e.g., particle diameter, charging state, ion exchange capacity and the like), the amount of electrolytes in the soil, the kind and the amount of microbial cells present in the soil. However, it is extremely difficult to foresee or control the degree of cohesion-precipitation of the dispersed soil which is the main cause of the variation for the recoveries of microbial cells.

Furthermore, recent advancements in microbiology have elucidated that a part of soil microorganisms (mostly bacteria) secrete a polymer-like substance to fix themselves to the soil particles or the like, and, in that state, they propagate and function. Since such microbial cells cannot be separated from the soil particles by a simple dispersing operation such as stirring, there is a problem in that the recovery of such microbial cells is low and resultant analysis does not reflect the actual microbial ecosystem.

As a solution of this problem, a method has been proposed in which the polymer-like substance is digested by using various enzymes, and then microbial cells are separated (Japanese Patent Application No. 5-307079). In this case, however, optimum reaction conditions, particularly pH, must be set according to the enzyme to be used. Therefore, under certain conditions, the cohesion of separated cells and soil particles and their resultant precipitation (cohesion-precipitation) may be accelerated; and the final recovery of microbial cells may decrease.

SUMMARY OF THE INVENTION

The present invention was made considering the problems of the above-mentioned conventional techniques.

An object of the present invention is to provide a method to recover soil microorganisms from soil in high amounts with high reproducibility.

Another object of the present invention is to provide a method to prevent cohesion-coprecipitation of microorganisms with soil particles.

Further object of the present invention is to provide a method to release the microorganisms attached to the soil particles through secreted polymer-like substance from the soil particles.

The above-mentioned objects can be achieved by the following present invention.

An aspect of the present invention is to provide a method for recovering soil microbial cells, which comprises the steps of suspending a soil sample containing microorganisms in an organic acid buffer solution of which the organic acid has 3 or more carbon atoms, and then separating the soil microorganisms into a supernatant of the suspension.

Another aspect of the present invention is to provide a method for recovering microorganisms from soil which comprises the steps of suspending a soil sample containing the microbial cells in an organic acid buffer solution of which the organic acid has 3 or more carbon atoms, separating the microorganisms into a supernatant of the suspension, adding a digesting enzyme to thus obtained microorganism suspension to degrade an insoluble polymeric organic substance secreted from the microbial cells, and then purifying and recovering the microbial cells from the resultant enzyme-treated microorganism suspension.

DETAILED DESCRIPTION OF THE PREFERRED EMBODIMENTS

In the present invention, a buffer solution (herein after, a buffer) comprising an organic acid of 3 or more carbon atoms is used at an early stage of a microbial cells recovering operation, to prevent cohesion-precipitation of microbial cells in a suspension, whereby the objective microbial cells can be finally recovered in a high yield with high reproducibility. Here, preferably, the microorganisms are bacteria, and the organic acid buffer comprises one or more buffers of which the main component is an organic acid or a salt of an organic acid. In particular, the organic acid buffer is a mixture of a citric acid solution and a sodium citrate solution having a buffer action at a pH value of 3.0 to 9.0.

Furthermore, the organic acid buffer is also responsive to the reaction conditions for a digesting enzyme, and so when the use of an organic acid buffer is combined with the enzyme treatment, the microbial cells can be recovered further in a higher yield. Preferably, the digesting enzyme is dissolved in a buffer comprising an organic acid of 3 or more carbon atoms, and the same organic acid buffer can be preferably used to dissolve the digesting enzyme and to suspend the soil sample.

Next, the present invention will be described in detail.

In the first place, the microorganisms in the present invention include bacteria, actinomyces, yeast, mold, mushrooms, fine algae, protozoans and the like, with no particular limitation on their habitats. The industrially useful microorganisms are bacteria.

In the present invention, a buffer comprising an organic acid of 3 or more carbon atoms is used from the first step of separation and recovery of the soil microorganisms to prevent the cohesion of the microbial cells, thus in subsequent recovery operations (e.g. separation of soil particles and microbial cells), the soil microorganisms can be recovered in a high yield with high reproducibility. When a conventional pH buffer such as a phosphate buffer is used, it is difficult to effectively prevent the cohesion of the microbial cells in the suspension. Only by using an organic acid buffer of 3 or more carbon atoms, the microbial cells can stay in an effectively dispersed state in the suspension.

In the present invention, as a dispersing medium to prepare the suspension, a buffer mainly comprising an organic acid of 3 or more carbon atoms or its salt is preferable. Examples of such organic acids include aspartic acid, γ-aminobutyric acid, citric acid, glycylglycine, glycine, succinic acid, serine, lactic acid, phthalic acid, fumaric acid, propionic acid, maleic acid, malonic acid and leucine. By using one or more of these organic acids or salts thereof, a buffer having a buffer action in a desired pH range can be prepared as the soil dispersing medium. When acetic acid which is the organic acid having 2 carbon atoms is used, the above-mentioned effect cannot be observed. The number of the carbon atoms in the organic acid is preferably in the range of 3 to 10, more preferably 4 to 6, and the buffer prepared from citric acid and salts thereof (particularly sodium citrate) is suitable.

Reagents used for this dispersing medium, e.g. an organic acid, should be of high purity, preferably a purity of about 99.8% or more, because contaminating salts in the reagent may cause the cohesion-precipitation of the microbial cells.

The pH of the buffer is in the range of acid to weak alkali (pH 3.0 to 9.0), preferably in the range of about pH 4 to 8. A higher or lower pH of the buffer may damage the microbial cells to be recovered making the subsequent analysis difficult. In addition, the pH is desirably in the range suitable for enzyme reaction. No particular limitation is set on the concentration of the buffer, but the range of about 50 to 100 mM is often effective to prevent the cohesion of the soil microorganisms. The volume of the organic acid buffer to be used is not particularly limited, so long as the soil sample can be sufficiently dispersed in the buffer. In general, the amount of the buffer is in the range of about 5 to 10 ml for 5 g of the soil (wet weight).

In general, soil scarcely precipitates in a soil dispersing medium which comprises the organic acid buffer, but some kinds of soil tend to cohere and precipitate in the presence of certain organic acids. Therefore, a dispersion and cohesion-precipitation test should be beforehand done to confirm the effectiveness of the organic acid to be used.

When the soil is dispersed in this kind of buffer, the cohesion of the microbial cells is prevented by the function of the organic acid buffer, so that usual operation to separate soil particles-microbial cells can be carried out subsequently. It is desirable to use the buffer as the dispersing medium until the microbial cells have completely been separated from the soil particles. For example, when an organic acid buffer is used to separate the microbial cells into the supernatant as the first step of the recovery operation of the microbial cells, and this supernatant is then subjected to a purification step using an enzyme solution or the like, the enzyme solution can be prepared using the same organic acid buffer as used in the first step. Furthermore, the buffer of this type can be used in the initial isolation operation of the DNA analysis method, the microbial particle detection method or the like. During the subsequent separation operation of soil particles and microbial cells, it should be avoided to add other salts, acids, alkalis or the like to the treatment solution, because such an addition may cause the cohesion and precipitation of the microorganism.

Next, as an example of the separation operation of soil particles and microbial cells following the recovery operation using the above mentioned organic acid buffer, the operation of enzymatic purification and recovery for the microbial cells will be described.

The enzyme treatment is described, for example, in Japanese Patent Application No. 5-307079, wherein a suspension of microbial cells which are bonded to a microorganism-supporting carrier or other microbial cells through the insoluble polymeric organic substance secreted by the microbial cells, is treated with an enzyme which can degrade the insoluble polymeric organic substance, to free the bonded microbial cells, and then the microbial cells are recovered and purified from the suspension utilizing the difference of specific gravity between the microbial cells, the carrier and the suspension medium, or utilizing the electrophoretic property of the microbial cells. The previously mentioned organic acid buffer can be used for the enzyme solution. When the enzyme treatment is used to release the microbial cells bonded to the microorganism-supporting carrier or the other microbial cells thorough the insoluble polymeric organic substance, the binding substance can be efficiently degraded, dispensing with a cultivation step. In addition, by the utilization of the difference of specific gravity or the electrophoresis of the microbial cells, the microbial cells in the suspension can be easily purified and recovered. Therefore, even a microorganism whose cultivation conditions are not known or which requires peculiar culture conditions can be easily separated and recovered in a short time from a suspension, a bioreactor fluid or the like in high yield and in high purity. Examples of the preferable digesting enzyme to be added include polysaccharide digesting enzymes, proteolytic enzymes and pectin digesting enzymes, such as cellulase, hemicellulase, glucuronidase, amylase, protease and pectinase. They can be used singly or in a combination of two or more thereof. The substance binding the microbial cells to the carrier or the like is the insoluble polymeric organic substance comprising various polysaccharides and proteins depending upon the kind of microorganisms, and when an enzyme which effectively degrades the organic polymer substance is selected and added, the separation efficiency of the microbial cells can be improved.

To purify and recover the microbial cells from a suspension obtained by enzyme treatment, a method based on the difference of specific gravity can be used, where the specific gravity of the enzyme-treated suspension is controlled so as to be equal to or higher than that of the microbial cells and lower than that of the microorganism-supporting carrier, and then the suspension is centrifuged to precipitate the microorganism-supporting carrier, followed by the recovery of the microbial cells from the resultant supernatant. For example, sucrose or cesium chloride can be dissolved as a solute to adjust the specific gravity of the enzyme-treated microorganism suspension to a value of 1.2 to 1.5. As another separation purification recovery method, there can be employed the electrophoresis of the microbial cells which comprises applying a predetermined DC voltage to the enzyme-treated microbial suspension, and then collecting the microbial cells migrated to the cathode or the anode. The number of the purified and recovered microbial cells in the suspension can be easily counted by a plate dilution method or a staining method.

Now, the present invention will be described in more detail with reference to examples. It should be noted that the scope of the present invention is not limited to these examples.

EXAMPLE 1

Recovery of Soil Microorganisms Using a Citrate Buffer (1) Preparation of citrate buffer A citrate buffer was prepared in a usual manner. That is to say, a 0.1M citric acid solution (21.01 g/l) was suitably mixed with a 0.1M sodium citrate solution (29.41 g/l, $C_6H_5O_7Na_3 \cdot 2H_2O$) to adjust pH to a desired value. In this example, pH was adjusted to 4.6 (citric acid:sodium citrate= 51:49), and the concentration was adjusted to 50 mM when used.

(2) Preparation of enzyme solution

As an enzyme source, AAP (abalone acetone powder from abalone eutrails, crude; made by Sigma Co., Ltd.) was used, and the enzyme solution was prepared as follows. In the first place, AAP was dissolved in the citrate buffer prepared in the above (1) at a ratio of 20 mg/ml. After sufficiently stirred and dissolved, it was centrifuged at 15000 rpm for 15 minutes in a refrigerated centrifuge to remove impurities. After the centrifugation, the resultant supernatant (enzyme solution) was passed through a filter having a pore size of 0.22 $\mu$m to remove bacteria and particles. Afterward, the obtained solution was used as the enzyme solution.

(3) Separation of bacteria from soil

First, in 12 spitz tubes (tapered tubes) 5 g (wet weight) portions of the test soil were put. The test soil was fine sand collected from the depth of 6 m of the ground. To each test tube, 9 ml portion of the citrate buffer (pH=4.6, 50 mM) prepared in (1) was added and the mixture was then stirred for about 30 seconds using a tube mixer (a vortex mixer) to sufficiently disperse the soil. After that, each dispersion was allowed to stand for 10 seconds to precipitate large soil particles, and 0.5 ml of the supernatant soil dispersion was transferred to a new spitz tube.

Next, 1 ml portions of the enzyme solution prepared in (2) were added to 6 tubes out of 12 tubes containing above prepared soil dispersion, and to each remaining 6 tubes, 1 ml of the above citrate buffer was added in place of the enzyme solution.

These samples were shaken at room temperature for 8 hours for the enzyme reaction, then 3.2 g of sucrose was added-to each tube and completely dissolved by shaking at 40° C. Each sample was transferred to a centrifuge tube, each test tube was washed with 1 ml of the citrate buffer and the washing was gently put on the high density sample layer in the centrifuge tube. These samples were subjected to centrifugation at 50000 rpm for 1.5 hours to separate the microbial cells from the soil particles based on specific gravity. After the ultracentrifugation, the supernatant containing the microbial cells was collected, and it was then diluted about 5 to 10 times to reduce the specific gravity, followed by centrifugation at 10000 rpm for 30 minutes to recover the microbial cells as a pellet.

(4) Count of microbial cells

The recovered microbial cells were dispersed in a saline to a suitable concentration, and stained with a fluorescent dye. As the fluorescent dye, ethidium bromide (EB) was used at a dye concentration of 20 $\mu$g/ml, and with a staining time of 1 hour. Afterward, this stained microbial dispersion was diluted or concentrated to a proper microorganism concentration, and the number of the microbial cells were counted using a flow cytometer.

(5) Results

Table 1 shows the results of the cell counts. As a control, microbial cells were counted in the same manner as described above except that phosphate buffer was used in place of the organic acid buffer. The numbers of the microbial cells largely vary in a range of $3.0 \times 10^3$ to $2.5 \times 10^5$ (cells/g wet soil) with low reproducibility. The count numbers themselves were small, thus recoveries were very low. On the other hand, in the samples in which the organic acid buffer was used with or without enzyme treatment, the variation of the cell numbers was small and the reproducibility was extremely good as clearly seen from the table 1. In addition, the recoveries were extremely high, although the recoveries of the enzyme treated samples were higher than those of the samples without treatment.

TABLE 1

[Number of microorganisms: cells/g (wet soil weight)]

| Sample No. | Enzyme Treatment | Number of Micro-organisms | Sample No. | Enzyme Treatment | Number of Micro-organisms |
|---|---|---|---|---|---|
| 1 | Present | $3.1 \times 10^7$ | 7 | Absent | $2.4 \times 10^6$ |
| 2 | Present | $3.0 \times 10^7$ | 8 | Absent | $2.5 \times 10^6$ |
| 3 | Present | $3.0 \times 10^7$ | 9 | Absent | $2.3 \times 10^6$ |
| 4 | Present | $3.2 \times 10^7$ | 10 | Absent | $2.4 \times 10^6$ |
| 5 | Present | $2.9 \times 10^7$ | 11 | Absent | $2.5 \times 10^6$ |
| 6 | Present | $3.0 \times 10^7$ | 12 | Absent | $2.4 \times 10^6$ |

EXAMPLE 2

Comparison Between Numbers of Microbial Cells in Soil Dispersions Using Different Buffers In this example, comparison was made between 4 kinds of buffers, i.e., saline, phosphate buffer (100 mM, pH 7.0), citrate buffer (50 mM, pH 4.6) and acetate buffer (100 mM, pH 5.0).

The components of the respective buffers are shown below.

(1) In 1 liter of the saline [PBS (−)]

| | |
|---|---|
| KCl | 0.2 g |
| KH$_2$PO$_4$ | 0.2 g |
| NaCl | 8 g |
| Na$_2$HPO$_4$ | 1.15 g |

(2) In 1 liter of the phosphate buffer (100 mM, pH=7.0)

| | |
|---|---|
| NaH$_2$PO$_4$ | 5.42 g |
| NaH$_2$PO$_4$.12H$_2$O | 21.87 g |

(3) In 1 liter of the citrate buffer (50 mM, pH=4.6)

| | |
|---|---|
| Citric acid | 5.36 g |
| Sodium citrate.H$_2$O | 7.21 g |

(4) In 1 liter of the acetic acid buffer (100 mM, pH=5.0)

| | |
|---|---|
| Acetic acid | 1.71 ml |
| Sodium acetate | 5.77 g |

As in Example 1 described above, 5 g of a sample soil was put into 10 ml of each buffer and stirred to obtain a soil dispersion. This soil dispersion was allowed to stand at room temperature, and the number of bacteria suspended in the dispersion was counted at certain time intervals. The counting method was a usual plate dilution method (aerobic culture, 2×TY medium). The results of the counts are shown in Table 2.

TABLE 2

[Number of microorganisms: cells/g (wet soil weight)]

| Time | Saline | Phosphate Buffer Solution | Citrate Buffer Solution | Acetate Buffer Solution |
|---|---|---|---|---|
| 10 sec | $8.5 \times 10^6$ | $8.5 \times 10^6$ | $8.5 \times 10^6$ | $8.5 \times 10^6$ |
| 1 min | $7.3 \times 10^6$ | $8.2 \times 10^6$ | $8.5 \times 10^6$ | $6.6 \times 10^5$ |
| 10 min | $2.6 \times 10^6$ | $7.0 \times 10^6$ | $8.5 \times 10^6$ | $1.8 \times 10^5$ |
| 30 min | $5.5 \times 10^5$ | $2.1 \times 10^6$ | $8.2 \times 10^6$ | $5.9 \times 10^4$ |
| 90 min | $6.7 \times 10^4$ | $3.4 \times 10^5$ | $7.7 \times 10^6$ | $3.9 \times 10^4$ |

As is clear from Table 2, when the organic acid buffer of 3 or more carbon atoms was used, the microorganism suspension was extremely stable, and the cohesion of the microbial cells scarcely occurred with the lapse of time.

According to the present invention, microorganisms can be collected or recovered from soil in a high recovery with good reproducibility. That is to say, when an organic acid buffer of 3 or more carbon atoms is used at an early stage of recovering operation, the cohesion and precipitation of the microbial cells in a suspension can be prevented. In consequence, the desired microbial cells can be finally recovered in a high yield with high reproducibility. Furthermore, the organic acid buffer also can cope with the conditions required for digesting enzyme treatment. Therefore, when the organic acid buffer is employed in combination with an enzyme treatment, the microorganisms can be recovered further in a higher yield from soil.

What is claimed is:

1. A method for recovering microorganisms from soil comprising the steps of:
   (a) suspending a soil containing microorganisms to be recovered in a citrate buffer solution comprising citric acid and a salt of citric acid to make a stable suspension; and
   (b) recovering the microorganisms from the stable suspension.

2. The method according to claim 1, wherein the buffer has a buffering action in a range of pH from 3.0–9.0.

3. The method according to claim 1, wherein the salt of citric acid is sodium citrate.

4. The method according to claim 1, wherein the step of recovering the microorganisms is conducted by employing centrifugation or electrophoresis.

5. The method according to claim 1, wherein the microorganisms are bacteria.

6. A method for recovering microorganisms from soil comprising the steps of:
   (a) suspending soil containing microorganisms attached to soil particles in a citrate buffer solution comprising citric acid and a salt of citric acid;
   (b) liberating the microorganisms from the soil particles suspended in the citrate buffer solution employing at least one enzyme selected from the group consisting of polysaccharide-digesting enzymes, proteolytic enzymes and pectin-digesting enzyme, wherein said citrate buffer solution is employed in an amount effective to prevent cohesion of the microorganisms and to provide a stable suspension of said liberated microorganisms; and
   (c) recovering the liberated microorganisms from the stable suspension by employing centrifugation or electrophoresis.

7. The method according to claim 6, wherein the buffer has a buffering action in a range of pH from 3.0–9.0.

8. The method according to claim 6, wherein the salt of citric acid is sodium citrate.

9. The method according to claim 6, wherein the microorganisms are bacteria.

10. A method for recovering microorganisms from soil comprising the steps of:
    (a) suspending a soil containing microorganisms attached to soil particles in a citrate buffer solution comprising citric acid and a salt of citric acid;
    (b) liberating the microorganisms from the soil particles suspended in the citrate buffer solution employing at least one enzyme selected from the group consisting of polysaccharide-digesting enzymes, proteolytic enzymes and pectin-digesting enzyme, wherein said citrate buffer solution promotes a stable suspension of the microorganisms liberated from the soil particles; and
    (c) recovering the liberated microorganisms from the stable suspension by employing centrifugation or electrophoresis.

11. The method according to claim 10, wherein the buffer has a buffering action in a range of pH from 4.0–8.0.

12. The method according to claim 10, wherein the salt of citric acid is sodium citrate.

13. The method according to claim 10, wherein the microorganisms are bacteria.

* * * * *